US010864315B2

(12) United States Patent
Fox et al.

(10) Patent No.: US 10,864,315 B2
(45) Date of Patent: Dec. 15, 2020

(54) MEDICAL CONSUMABLE STORAGE, DISPENSING, AND DISPOSAL SYSTEM

(71) Applicant: Drexel University, Philadelphia, PA (US)

(72) Inventors: Carson S. Fox, Philadelphia, PA (US); Richard M. Dambra, Stormville, NY (US); Amy L. Throckmorton, Cherry Hill, NJ (US)

(73) Assignee: Drexel University, Philadelphia, PA (US)

( * ) Notice: Subject to any disclaimer, the term of this patent is extended or adjusted under 35 U.S.C. 154(b) by 0 days.

(21) Appl. No.: 16/254,122

(22) Filed: Jan. 22, 2019

(65) Prior Publication Data

US 2019/0224404 A1    Jul. 25, 2019

Related U.S. Application Data

(60) Provisional application No. 62/620,498, filed on Jan. 23, 2018.

(51) Int. Cl.
| | |
|---|---|
| *B65D 83/02* | (2006.01) |
| *A61M 5/00* | (2006.01) |
| *A61M 5/32* | (2006.01) |
| *B65D 83/04* | (2006.01) |

(52) U.S. Cl.
CPC ............ *A61M 5/002* (2013.01); *A61M 5/008* (2013.01); *A61M 5/3205* (2013.01); *B65D 83/02* (2013.01); *A61M 2005/004* (2013.01); *B65D 83/0454* (2013.01); *B65D 2583/0486* (2013.01)

(58) Field of Classification Search
CPC ................. A61M 5/002; A61M 5/008; A61M 2005/004; B65D 83/02; B65D 83/0454; B65D 2583/0486; A61B 2050/3004; A61B 2050/3006; A61B 2050/314; A61B 50/3001; A61B 50/362
USPC ......................... 206/366; 220/506, 529, 908
See application file for complete search history.

(56) References Cited

U.S. PATENT DOCUMENTS

| | | | |
|---|---|---|---|
| 4,586,614 A | 5/1986 | Ger | |
| 5,193,678 A | 3/1993 | Janocik et al. | |
| 5,335,783 A | 8/1994 | Sinn | |
| 5,508,681 A | 4/1996 | Nelson et al. | |
| 7,815,046 B2 * | 10/2010 | Sansoucy | A61M 5/002 206/366 |
| 8,113,349 B2 | 2/2012 | Sansoucy et al. | |
| 8,418,851 B2 | 4/2013 | Culligan et al. | |
| 8,576,076 B2 | 11/2013 | Morris et al. | |
| 9,451,949 B2 | 9/2016 | Gorek et al. | |
| 2002/0049560 A1 | 4/2002 | Reff | |
| 2004/0129591 A1 | 7/2004 | Koseki | |
| 2006/0243618 A1 * | 11/2006 | Brown | A61M 5/3205 206/366 |

(Continued)

FOREIGN PATENT DOCUMENTS

WO    WO2009136193    11/2009

*Primary Examiner* — Gene O Crawford
*Assistant Examiner* — Ayodeji T Ojofeitimi
(74) *Attorney, Agent, or Firm* — Joseph E. Maenner; Maenner & Associates, LLC (57) ABSTRACT

A suture storage, dispensing, and disposal device is disclosed. The device provides a method for storing sutures or other medical consumables, dispensing the sutures or other medical consumables, and disposing of used sutures or other medical consumables.

18 Claims, 12 Drawing Sheets

(56) References Cited

U.S. PATENT DOCUMENTS

| | | | | |
|---|---|---|---|---|
| 2006/0243619 A1* | 11/2006 | Brown | ................ | A61M 5/3205 |
| | | | | 206/366 |
| 2006/0243635 A1* | 11/2006 | Sullivan | ............. | A61B 17/3217 |
| | | | | 206/571 |
| 2009/0114671 A1* | 5/2009 | Finnestad | ............... | A61B 50/30 |
| | | | | 221/102 |
| 2010/0084293 A1* | 4/2010 | Erickson | ............. | A61M 5/3205 |
| | | | | 206/366 |
| 2010/0084406 A1* | 4/2010 | Erickson | ............. | A61M 5/3205 |
| | | | | 220/557 |
| 2012/0265336 A1 | 10/2012 | Mallett et al. | | |
| 2015/0108021 A1 | 4/2015 | Erickson et al. | | |
| 2015/0351850 A1 | 12/2015 | McElhinny et al. | | |

\* cited by examiner

MEDICAL CONSUMABLE STORAGE, DISPENSING, AND DISPOSAL SYSTEM

CROSS-REFERENCE TO RELATED APPLICATION

The present application claims the benefit of U.S. Provisional Patent Application Ser. No. 62/620,498, filed on Jan. 23, 2018, which is incorporated herein by reference in its entirety.

BACKGROUND OF THE INVENTION

Field of the Invention

The present invention relates to a device to store, dispense, and dispose of consumable medical equipment, such as needles, sutures, sponges, gauze pads, and other medical devices that are used and disposed of during a medical procedure.

Description of the Related Art

More than 600,000 needle stick injuries due to sutures are reported to occur each year in hospitals across the United States; this statistic does not include Urgent Care locations or Emergency Management Systems. Over 5 million health care professionals are at risk of needle stick injuries, which risks direct exposure to bloodborne pathogens. Approximately 40% of sticks occur after the needle usage, and 15% occur after needle disposal. The average cost to the hospital per needle stick is over $5,000, and it is estimated that there is, on average, 1 needle stick per every 10 surgical procedures. For a large hospital system, such as Hahnemann Hospital, the costs of treatment and addressing the needle sticks due to sutures could exceed $4 million per year.

It is estimated that 5-12 sutures are wasted per surgery to needled sticks or to being simply used. Moreover, suture needles are misplaced or lost in the rapid response that is required for some procedures and patient stabilization. It is estimated that 3,000 sutures are misplaced per year. Approximately 10% of these needles are in fact left in patients, which results in lawsuits and treatment expense that are estimated to exceed $25,000,000 per year.

To address the need for more control and dispensing power over the needles and sutures, as well as other medical consumables, a storage, dispensing, and disposal system is needed.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings.

DETAILED DESCRIPTION OF THE INVENTION

In the drawings, like numerals indicate like elements throughout. Certain terminology is used herein for convenience only and is not to be taken as a limitation on the present invention. The terminology includes the words specifically mentioned, derivatives thereof and words of similar import. The embodiments illustrated below are not intended to be exhaustive or to limit the invention to the precise form disclosed. These embodiments are chosen and described to best explain the principle of the invention and its application and practical use and to enable others skilled in the art to best utilize the invention.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments necessarily mutually exclusive of other embodiments. The same applies to the term "implementation."

As used in this application, the word "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion.

Additionally, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

As shown in the Figures, the present invention is a device 100 that stores, dispenses, and disposes of sutures/suture needles. The dispensing aspect of device 100 includes counting or tracking sutures/suture needles that are dispensed from device 100. Device 100 can be configured to take pre-packaged sutures in their native packaging or to take cartridges designed specifically to fit device 100.

Device 100 is used to store, dispense, and dispose of sutures, needles, and other consumables to a circulating nurse or surgeon in a surgical and/or hospital setting. For ease of discussion, only sutures will be discussed, although other consumables can be stored, dispensed, and disposed of with device 100. Device 100 provides:

the sterile presentation of sutures one-at-a-time to a circulating nurse or surgeon;

the self-opening of a suture storage container upon dispensing;

the retraction and sterile disposal of the packaging that the suture is presented in;

the safe disposal of sutures through a sealing system;

a counting system which keeps track of sutures dispensed and returned;

an alert system which can be customized to inform the user when a suture is out for an extended period of time; and the storing and cataloging of inventory data used for billing.

Referring to FIGS. 1-7, device 100 includes six bays 102, 104, 106, 108, 110, 112 for fresh, unused suture storage and dispensing. While six bays 102-112 are provided, those skilled in the art will recognize that more or less than six bays 102-112 can be used. Further, while all bays 102-112 can store and dispense the same product (e.g., same size sutures), those skilled in the art will recognize that bays 102-112 can hold different types and/or sizes of product (e.g., different size sutures, sutures, gauze pads, etc.). Bays 102-112 are covered by a front cover plate 114 that is removably attached to the front of device 100. In the event of an electrical power failure or other malfunction that prevents or restricts the dispensing of consumables, cover plate 114 can be easily and quickly removed to allow access to sutures stored inside device 100.

Bays 102-112 can be individually inserted into and removed from device 100 to reload sutures into device 100. Bays 102-112 can be provided as a sealed bay, pre-stocked with sutures or, alternatively, bays 102-112 can be autoclavable and re-fillable.

Each bay 102-112 can be identical, so only bay 102 will be described herein.

Figure 1:
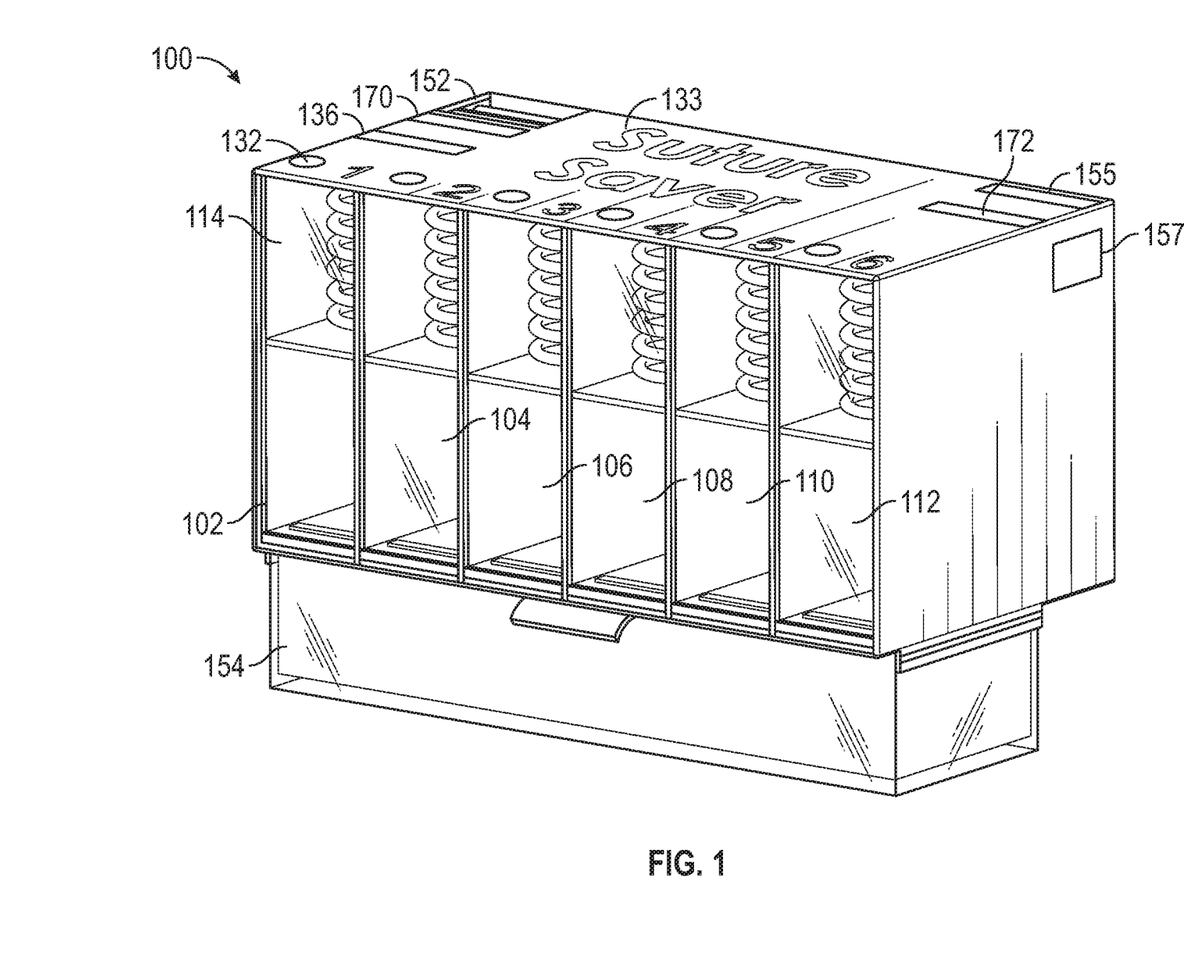
FIG. 1 is a right perspective view of a suture storage, dispensing, and disposal device according to an exemplary embodiment of the present invention.
Figure 2:
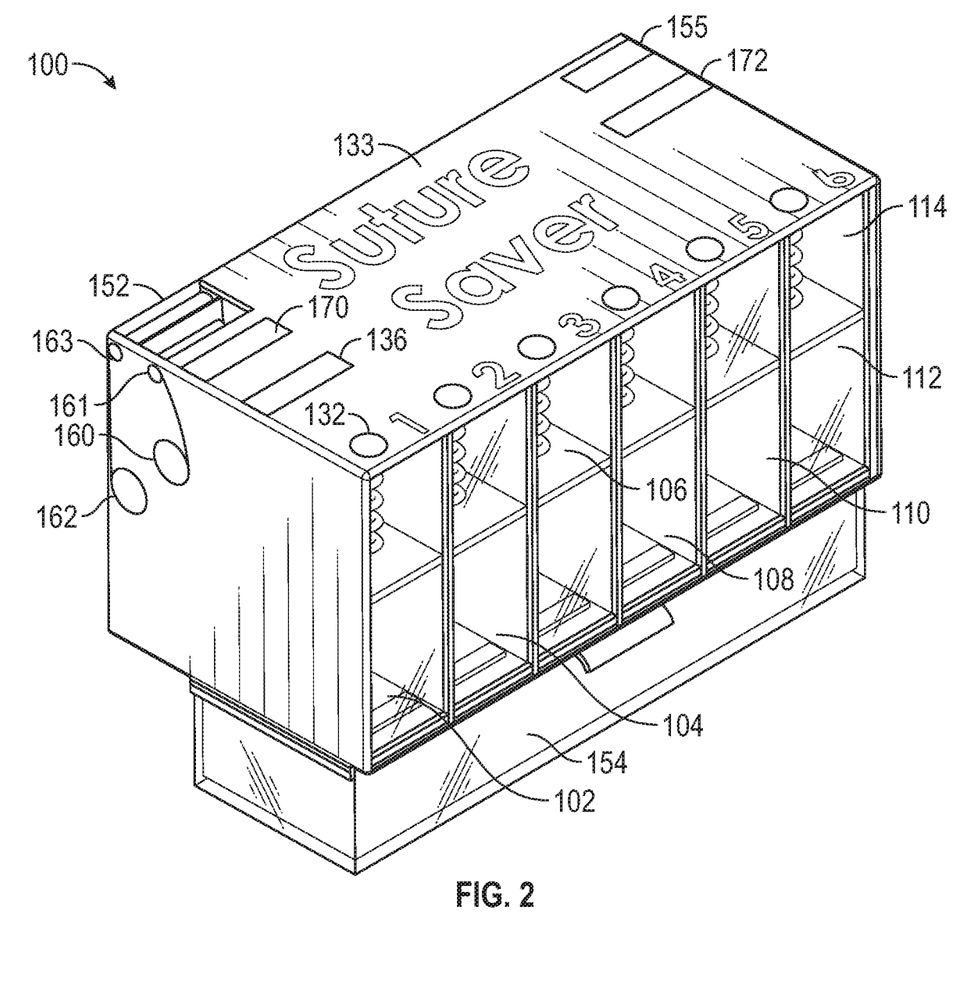
FIG. 2 is a left perspective view of the device shown in FIG. 1.
Figure 3:
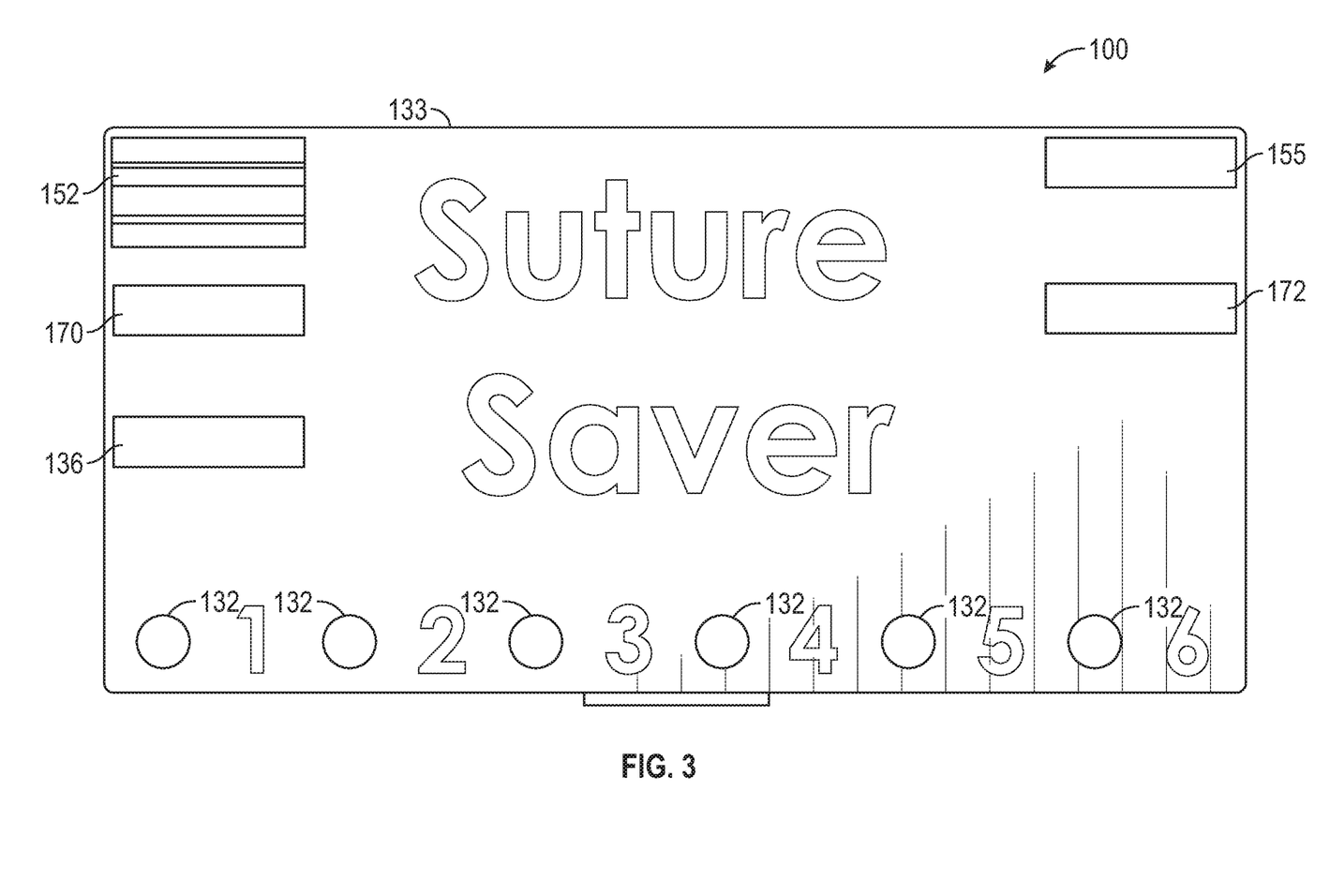
FIG. 3 is a top plane view of the device shown in FIG. 1.
Figure 4:
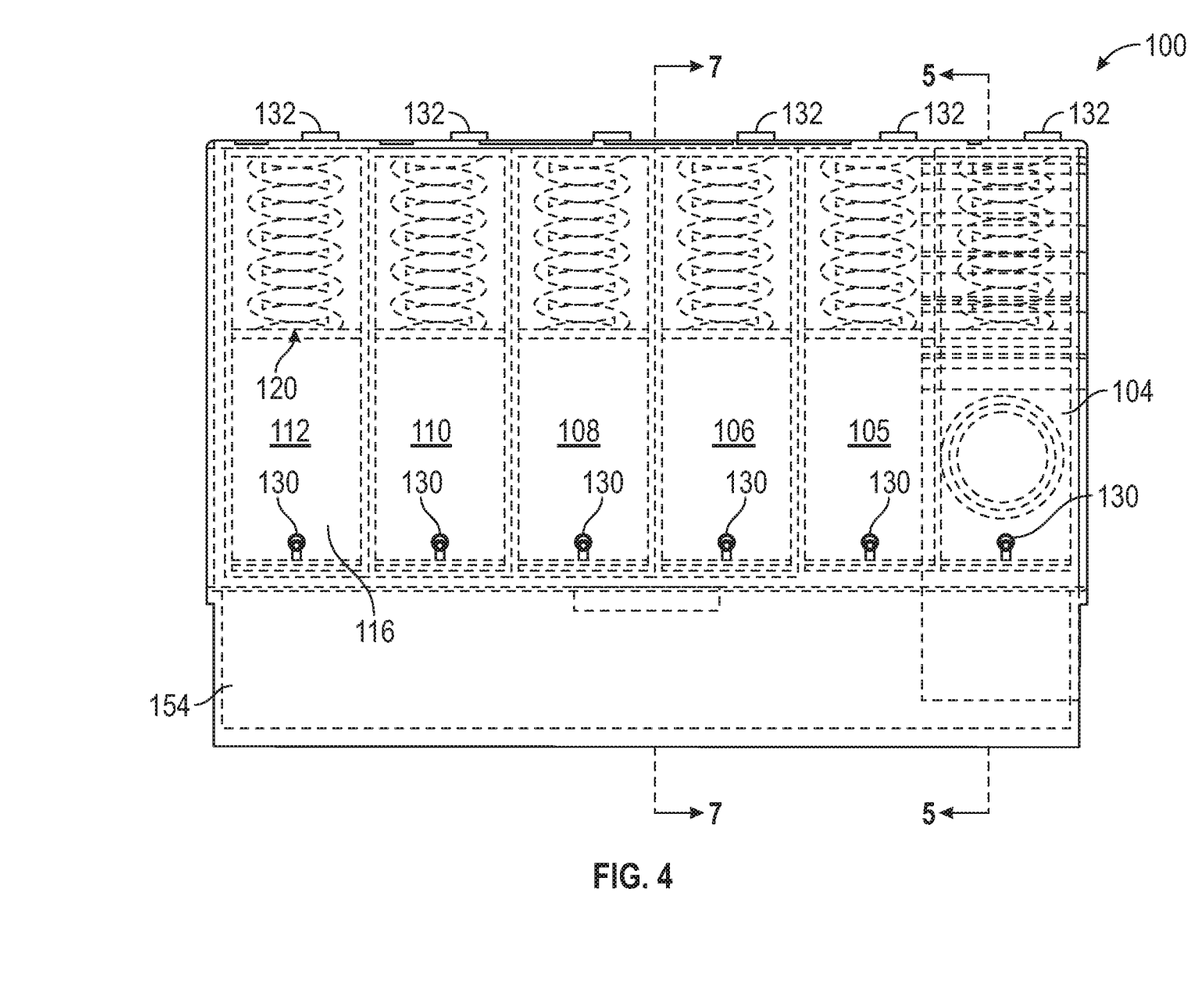
FIG. 4 is a rear elevational view of the device shown in FIG. 1.
Figure 5:
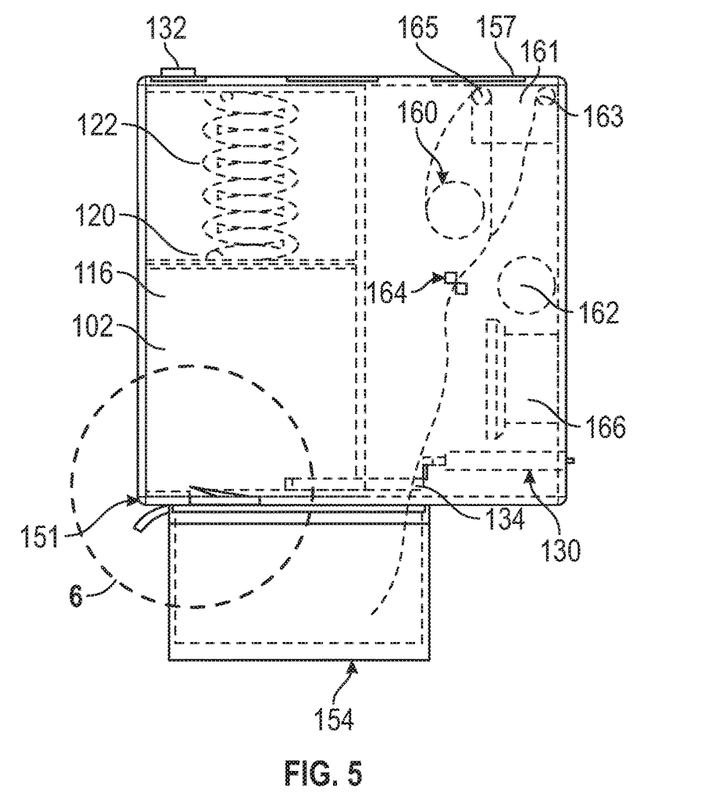
FIG. 5 is a sectional view of the device shown in FIG. 1, taken along lines 5-5 of FIG. 4.

Referring specifically to FIG. 5, bay 102 includes a storage area 116 for storing a stack of suture packages 50. A spring hopper 120 is located above storage area 116 and includes a biasing member 122 in the form of a helical spring to bias the sutures downward for dispensing from bay 102.

Referring to FIG. 5, a push bar 130 is used to push a suture package 50 (shown in FIG. 8) out of device 100. Push bar 130 is operatively connected to a start button 132 on the top of bay 102. Start button 132 is operatively connected to a motor (not shown) that rotates a sleeve 134. Sleeve 134 includes an internal threaded connection that mates with an external connection on push bar 130 such that, as sleeve 134 rotates due to rotation of its motor, push bar 130 is advanced from sleeve 134. Push bar 130 contacts suture package 50, pushing suture package 50 out of device 100.

As suture package 50 is being dispensed through an opening 151 in the front of device 100, the lid 52 of suture package 50 engages the front of device 100, peeling lid 52 from suture package 50, revealing the suture for removal from suture package 50. After suture package 50 is dispensed from device, the motor reverses direction and rotates sleeve 130 to retract push bar 130 into sleeve 134 for dispensing on another suture package 50.

Figure 6:
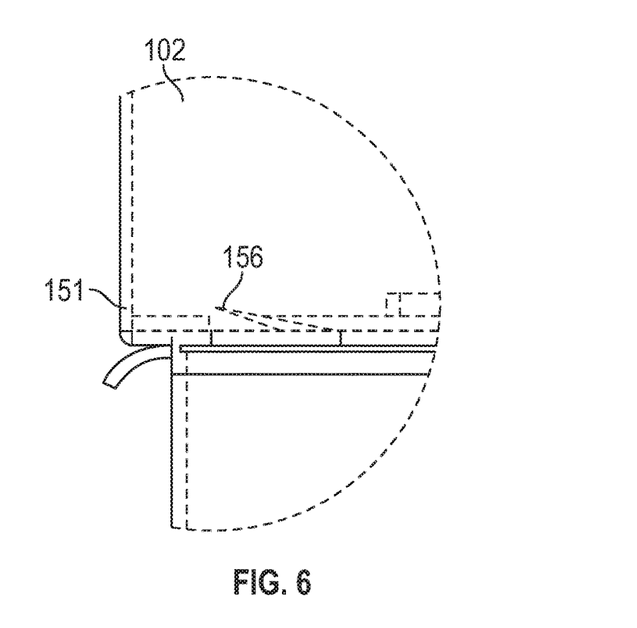
FIG. 6 is an enlarged portion of the device shown in FIG. 5, taken along circle 6 shown in FIG. 5.

The now-empty suture package 50 can be pushed into a waste disposal drawer 154. Waste disposal drawer 154 is located below bay 120 for receiving empty suture packages 50, along with used sutures 52, as will be discussed later herein. Referring to FIG. 6, a false edge 156 in the bottom of bay 120 provides communication between bay 120 and waste disposal drawer 154 so that empty suture package 50 can fall through false edge 156 and into waste disposal drawer 154. When waste disposal drawer 154 is full, waste disposal drawer 154 can be removed from device 100, emptied, and re-inserted into device 100.

Start button 132 is operatively connected to a processor (not shown) that includes a program to recognize and store a count of the item that was dispensed, as well as display the number of dispensed product in a digital display 136 on top of device 100. The processor can also store the time at which suture package 50 was dispensed from device 100. Further, the processor can determine when a suture supply is running low and provide a sensory indication to a user to restock any/all of bays 102-112. While a physical button 132 is shown in the Figures, those skilled in the art will recognize that button 132 can be part of a touch display screen that can make up all or part of the top surface 133 of device 100. Optionally, a sterile soft polymer cover can be applied over device 100. Still alternatively, a "peel and stick" adhesive backed transparent polymer sheet cover can be applied over at least top surface 133 of device. These covers limit the possibility of bodily fluids or other contaminants from contaminating device 100. If bodily fluids engage the cover, after a procedure, the cover can be removed and sterilized or replaced.

Once the user has finished with their suture 52, the used suture 52 can be dropped into a suture disposal mechanism 150 in device 100 for safe disposal and reliable counting. The following subcomponents make up suture disposal mechanism 150:

Opening 152 for product disposal with activation sensor.
Rollers with Plastic 160, 162
Heat Sealing Mechanism 164
Digital Display
Counting Sensor 166

The suture 52 is dropped into an opening 152 on top of device 100. Once the suture 52 passes by an activation sensor 161 located proximate to opening 152 and operatively connected to the processor, the mechanism of sealing the suture 52 begins.

Figure 7:
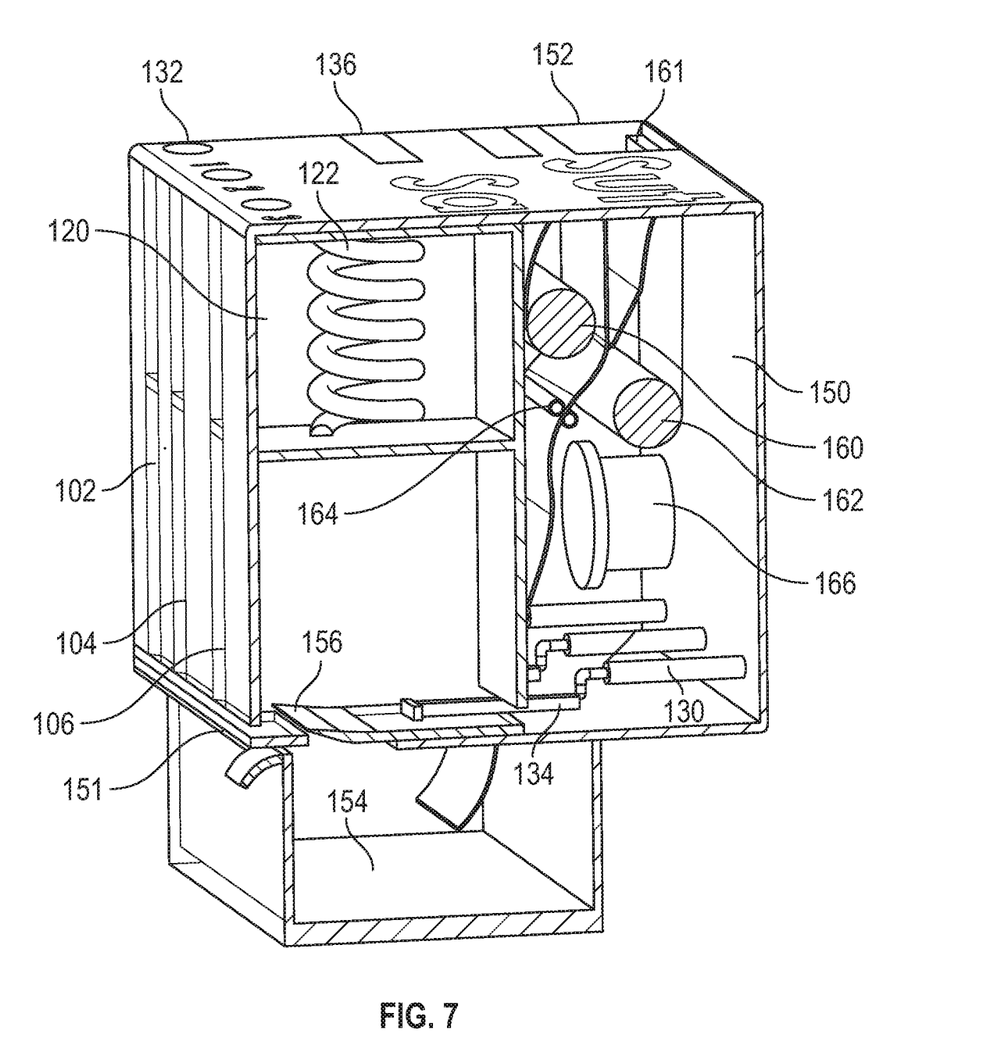
FIG. 7 is a perspective view, in section, of the device taken along lines 7-7 of FIG. 4.

Referring to FIGS. 5-7, rollers 160, 162 each retain a roll of plastic. Rollers are operatively connected to roller motors (not shown) that are in turn operatively connected to the processor. Guide rollers 163, 165 guide unrolled plastic from rollers 160, 162, respectively, to either side of opening 152, forcing the suture 52 between the rolls of plastic and keeping the suture 52 between the plastic for subsequent sealing between the plastic.

When activation sensor 161 senses the presence of a suture 52, rollers 160, 162 unroll their respective plastic, with suture 52 sandwiched therebetween, pulling the used suture 52 through a heat sealing mechanism 164. As the plastic from the rollers 160, 162 is pulled through heat sealing mechanism 164 with the suture 52 between the sheets of plastic, each suture 52 is individually sealed in between the sheets of plastic, forming a pouch 167. At this point the suture 52 has been isolated and is safe from easily sticking a user. After the suture 52 is sealed, the sealed suture 52 passes by a counter 166 which identifies the suture 52 and counts suture 52. Although counter 166 is shown in FIG. 5 as being located after suture 52 is sealed, those skilled in the art will recognize that counter 166 can be located upstream of sealing mechanism 164 to count used suture 52 prior to being sealed.

Heat sealing mechanism can seal suture 52 such that the entire pouch 167 around suture 52 is sealed or, alternatively, only the perimeter of pouch 167 is sealed. Optionally, in addition to sealing pouch 167, a printer 180 can be provided to print identifying information on pouch 167. Printer 180 can print identifying indicia, such as the time/date that suture 52 was placed into suture disposal mechanism 150, along with any patient identifying information, to be able to track sutures 52 used on a particular patient, along with the time when suture 52 was disposed. A roller 180 disposed across pouch 167 from printer 180 can provide a solid surface for pouch 167 as the identifying indicia is being printed on pouch 167.

In an exemplary embodiment, the counting system can use infrared signatures, camera identification, or ultra violet signatures to identify not just that a suture 52 has passed but what kind of suture or needle has passed. This information is important to identify what kind and the number of items have not been returned, i.e., if device 100 is dispensing four kinds of sutures and two gauges of needles, and more than one of these items is out at once, device 100 will be able to display to the user which item has not been returned.

Once the suture is sealed 52 and counted, the suture 52 is dispensed into waste disposal drawer 154, along with suture package 50 as described above.

As discussed above, counter 166 keeps track of what has been returned. Once the item has been returned, a digital display 170 shows the number of product returned. The digital display 172 then shows the amount of sutures 52 still out by taking a difference between displays 136 and 170. The program will take the difference of the sutures 52 dispensed and returned for each item and continually provide a value on a digital display 172 above each item.

In the event that electrical power is lost or device 100 fails to operate during a procedure, in addition to removing front plate 114, a secondary disposal drop slot 155 can be provided in top surface 133 for the sutures to drop into a drawer 157 (shown in FIG. 1) that can be removed from the side of device 100. After power is restored or device 100 is fully operational, the sutures can be manually removed from drawer 157 and dropped into opening 152 to be counted and sealed for ultimate disposal.

As sutures and needles can be lost in surgery, the need for a reliable and safe counting system is necessary. Some surgeries can last for many hours and when a needle or suture is misplaced can be very difficult to locate if it is unknown when the item was misplaced. Device 100 can include an alert system that can be customized to inform the user when a needle or suture is out for a predetermined period of time.

By way of example, the user can set a custom time frame to be alerted when the product is not returned. An alert, such as a sound or other notification, from device 100 will tell the user that a particular item has not been returned and if it has been misplaced there will be a specific time frame where it could have been misplaced, making it easier to locate the lost item. The user will know which item is misplaced by having the digital display light up for that item.

While the storage, dispensing, and disposal aspects of device 100 discussed above contemplate a singular unit, those skilled in the art will recognize that the storage and disposal aspects can be separate sub-units that can be removed from device 100 and replaced with replacement sub-units. For example, when disposal drawer 154 is full, disposal drawer 154 can be removed from device 100 and the sutures inside disposal drawer 154 can be deposited into a sharps waste container and replaced into device 100. Alternatively, the entire disposal drawer 154 can be disposed on in a sharps disposal, and a new (empty) disposal drawer 154 can be inserted into device 100.

Device 100 can also be used for the storing and cataloging of inventory data used for billing. By way of example, the counting system described above stores the amount of product dispensed during a specific surgery and can feed this information to a computer in a basic text or spreadsheet format. This will allow for the establishment or user to easily charge the patient for the items used. It is very common in all the confusion of procedures that items are used and no one is charged for them, this is a loss for the user and/or establishment. This data can also be used by the establishment for reordering supplies and keeping a consistent inventory at all times.

Figure 8:
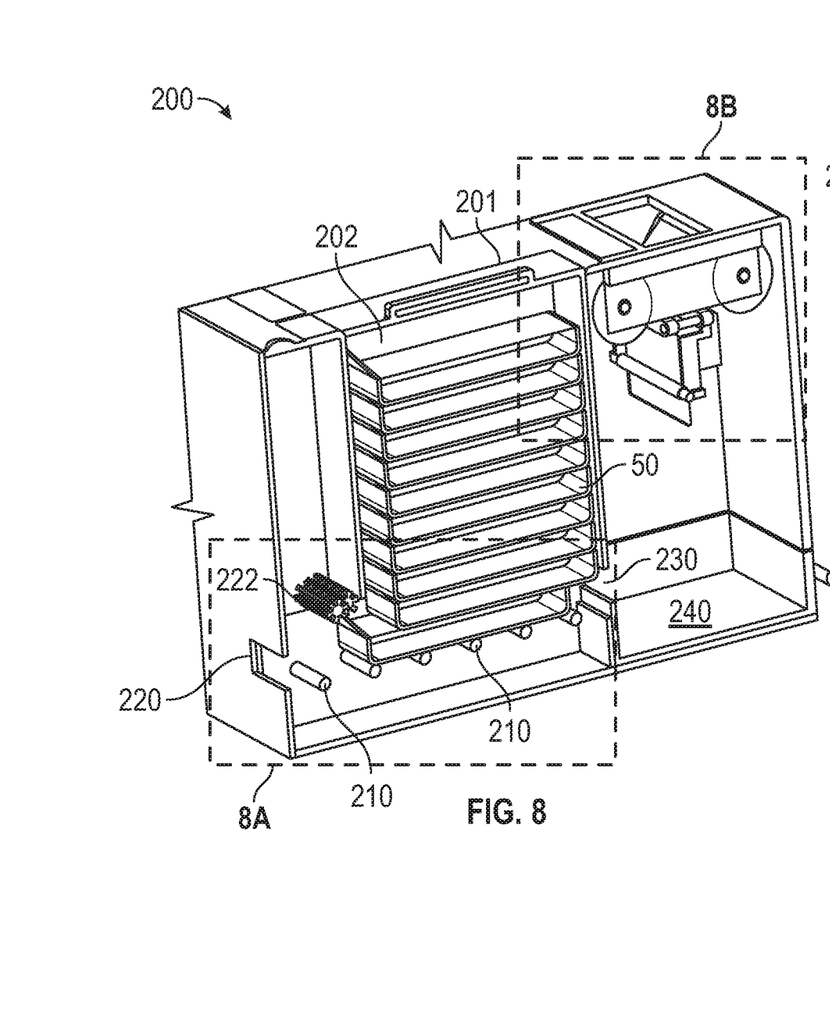
FIG. 8 is a perspective view of a suture storage, dispensing, and disposal device according to an alternative exemplary embodiment of the present invention.
Figure 9:
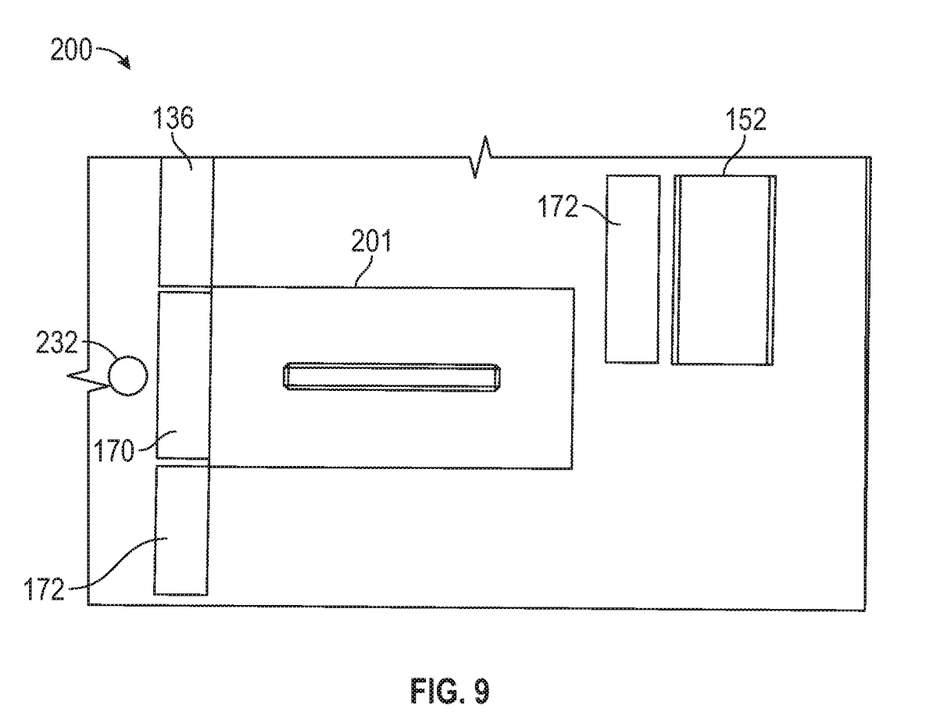
FIG. 9 is a top plan view of the device shown in FIG. 8.

An alternative embodiment of a device 200 that stores, dispenses, and disposes of sutures/suture needles is shown in FIGS. 8 and 9. Device 200 provides an alternative method for dispensing the sutures. Suture packages 50 for dispensing are stocked by removing a lid 201 on top of device 200 and feeding the sutures into a bay 202 in a manner consistent with FIG. 8. Once the suture packages 50 are loaded, gravity feeds suture packages 50 into the opening mechanism. Optionally, although not shown, a biasing member such as biasing member 122 can also be used, attached to lid 201 to bias suture packages 50 down once suture packages 50 are loaded.

Suture packages 50 are fed vertically down to an extracting device, which can be a set of rollers 210. Rollers 210 are all active rollers, operatively connected to and run by a single motor 212, shown in the background of FIG. 8. All of rollers 210 are attached with a belt (not shown) to make all rollers 210 actively move with operation of motor 212. Alternatively, rollers 210 could also run on motor 212 utilizing gears (not shown). It may also not be necessary to have all of rollers 210 active. Optionally, additional rollers 210 can also be added above lowest suture package 50 to ensure smooth passage through device 200. Such additional rollers can be active or passive. Other means for advancing suture package 50 are described below.

Once rollers 210 move suture package 50 forward for dispensing towards dispensing slot 220, the angled lid 52 on suture package 50 is rolled into a gear system 222, comprised of a first gear roller 224 and a second gear roller 226. One or both of gear rollers 224, 226 can be run by an independent motor (not shown). Once the lip 54 of lid 52 is secured in rollers 224, 226, rollers 210 will continue to roll the base of the suture package 50 forward through dispensing slot 220. As suture package 50 moves toward dispensing slot 220, lid 52 is pulled backward, off of suture package 50, exposing the contents of suture package 50 as suture package 50 rolls through dispensing slot 220. The opened suture package 220 with sterile contents is presented outside of the device 200 for the user to take from open suture package 50.

Once a suture is taken from suture package 50, package guide and gear rollers 210 will reverse, pushing suture package 50 and lid 52 through a package disposal slot 230. Package disposal slot 230 leads to a waste disposal unit 240 where suture package 50 and the sealed and used sutures are fed.

Other mechanisms, practical or impractical, can be used to open packaging or provide sterile presentation of needles and sutures. These mechanisms include the following:

a. A pneumatic system that suctions the top of a plastic or metal packaging to open it and present the contents.

b. A cutting mechanism can be used to remove part of the packaging and to present contents to the user.

c. A two roller gear system to pull one flap of packaging down and one flap of packaging up to split packaging and present the sterile contents.

d. The roller gear system can be substituted for any material or roller texture that will reliably take hold the packaging flaps or tops.

e. A magnet system could potentially be used by placing small amounts of metal into the packaging, making it easier to control the packaging and opening it.

Figure 8A:
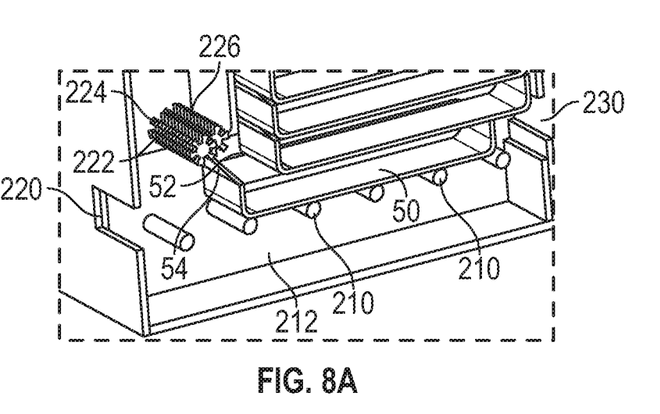
FIG. 8A is an enlarged view of a suture dispensing device taken from box 8A of FIG. 8.
Figure 8B:
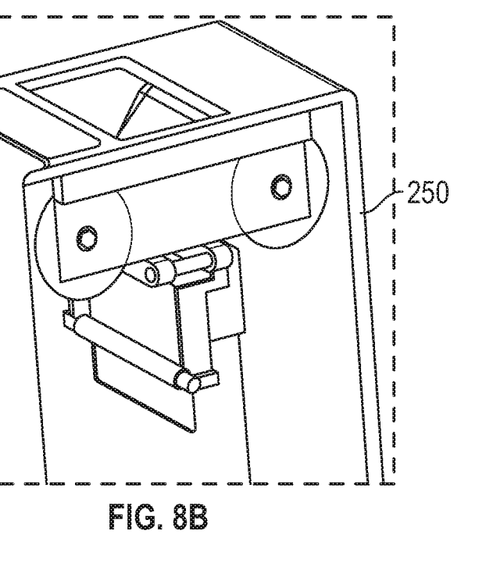
FIG. 8B is an enlarged view of a suture disposal device taken from box 8B of FIG. 8.

A suture disposal mechanism 250, similar to suture disposal mechanism 150 described above, and shown in FIG. 8, can be used to dispose of and count used sutures. The elements of suture disposal mechanism 150 are identified in FIG. 8A with respect to suture disposal mechanism 250. Additionally, a digital display system, similar to displays 136, 170, 172 on device 100 can be used with device 200.

Figure 10:
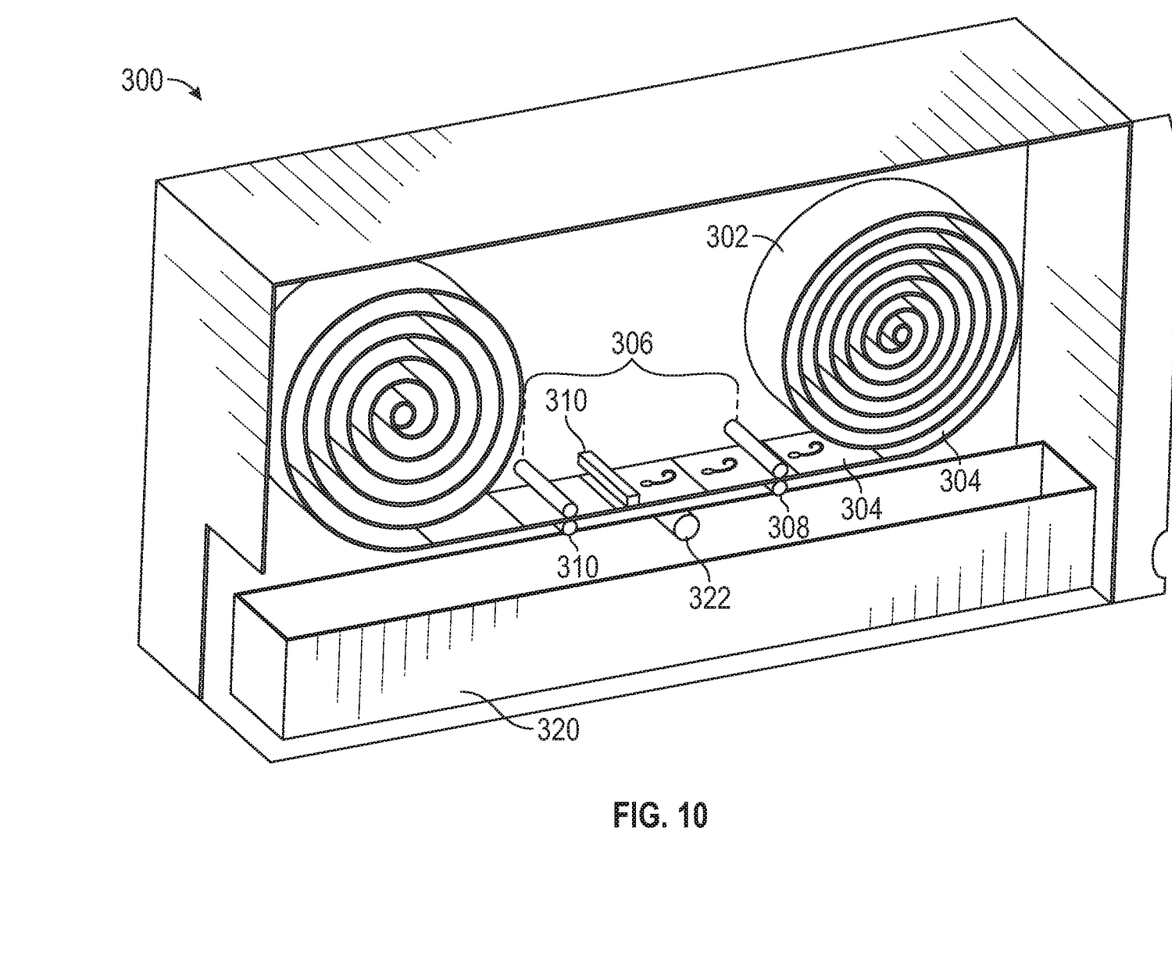
FIG. 10 is a perspective view of a suture storage, dispensing, and disposal device according to an alternative exemplary embodiment of the present invention.

FIG. 10 shows an alternative embodiment of a storage, dispensing, and disposal device 300 according to the present invention. Device 300 is similar to device 200 but, instead of individual suture packages 50, sutures 52 are provided in a sealed roll 302 with each suture 52 sealed in its own pouch 304. A dispensing mechanism 306 includes an upstream roller assembly 308 that peels open each pouch 304 as pouch 304 passes through roller assembly 306.

A cutter 310 cuts open pouch 304 to dispense suture 52. Cutter 310 can be a "chop" blade that engages pouch 304 along a plane generally perpendicular to the direction of travel of pouch 304. Alternatively, cutter 310 can "sliding" blade that moves in a direction transverse to the direction of pouch 304 and slices pouch 304 as slicing blade travels.

A downstream roller assembly 312 pulls empty pouch 304 along to a roller (not shown) to wrap empty pouches 304 and advance roll 302 to allow the next suture 52 to be dispensed.

Each suture 52 gravity drops from its open pouch 50 into a bin 320 located below dispensing mechanism 306. An optical device 322 can determine when suture 52 dropped into bin 320 and in turn operate a motor (not shown) to push bin 320 out of device 300 so that the suture 52 in bin 320 can be picked up and used. For example, a roller system such as rollers 210 disclosed above can be used to roll bin 320 out of device 300.

Figure 11:
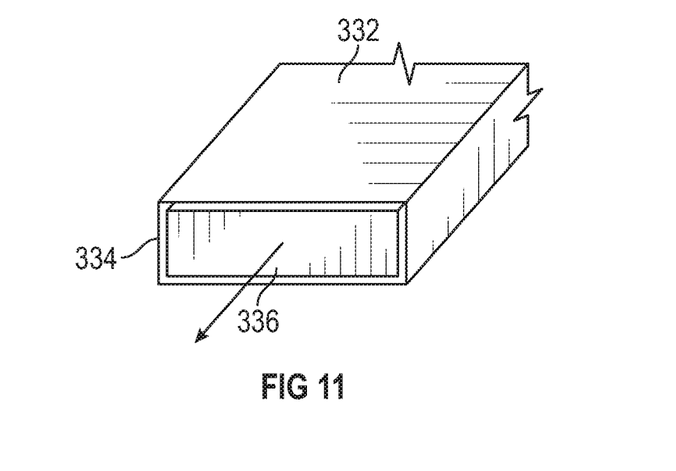
FIG. 11 is a perspective view of a closed suture bin according to an exemplary embodiment of the present invention.
Figure 11A:
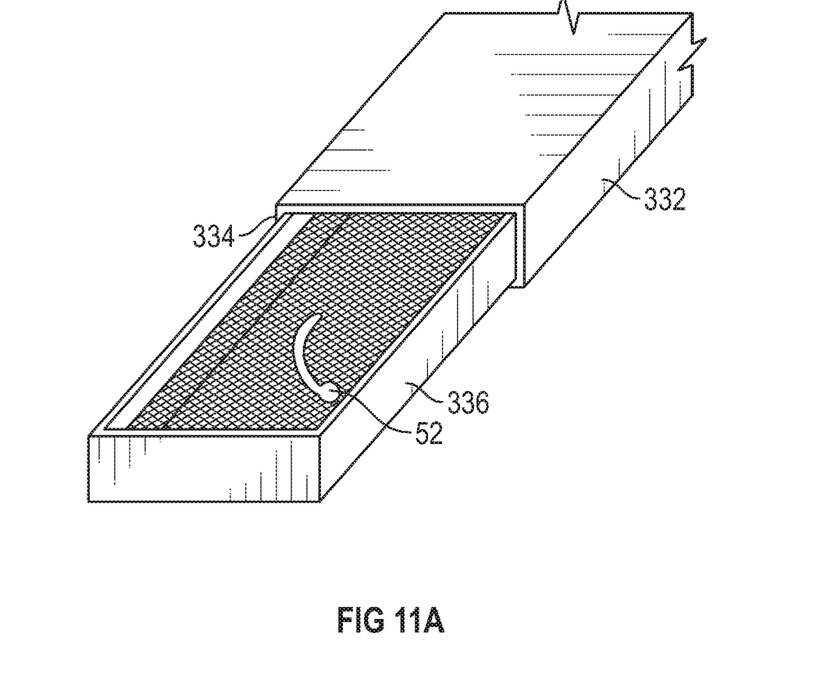
FIG. 11A is a perspective view of the suture bin of FIG. 11 in an open position.

Alternatively, a spring biased bin assembly, such as bin assembly 330, shown in FIGS. 11 and 11A, can be used instead of bin assembly 320. Bin assembly 330 includes a housing 332 having a front opening 334. A bin 336 is disposed inside housing 332 and is spring-biased to open by pushing bin 336 inwardly into housing 332 and releasing bin 334. A spring (not shown) in housing 332 pushes bin 336 at least partially out through front opening 334 so that medical personnel can reach into bin 336 and pull out suture 52 from bin 336.

Alternatively, bin 336 can be pushed outwardly from housing 332 be a mechanism similar to push bar 130 discussed above.

Figure 12:
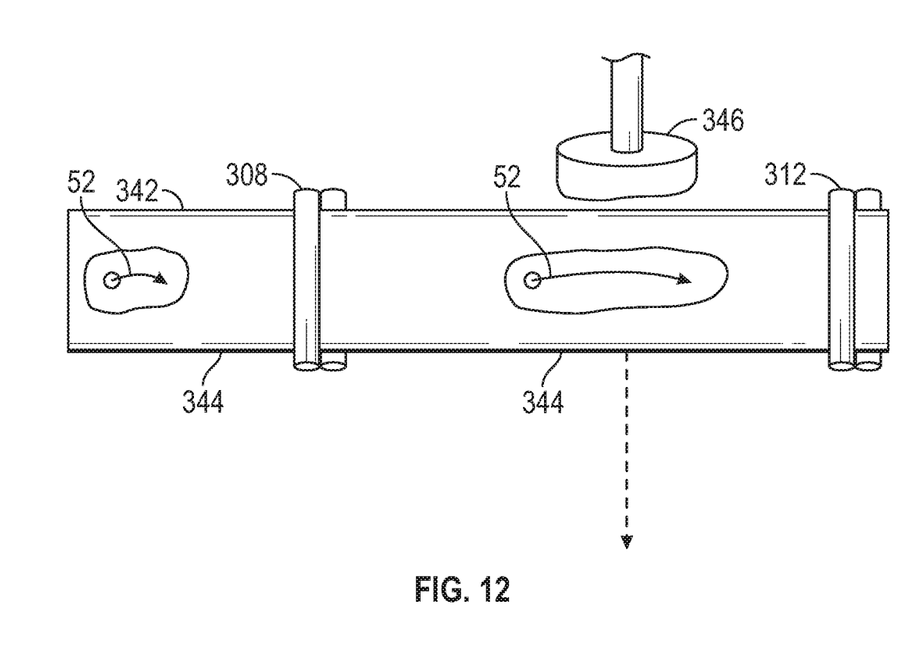
FIG. 12 is a perspective view of a mechanism for dispensing sutures according to an exemplary embodiment of the present invention.

In an alternative embodiment, shown in FIG. 12, instead of using cutter 310 described above, pouch 304 can be similar to a blister pack that us used for storing and dispensing pills or capsules. A roll 342, similar to roll 302, can be provided with sealed pouches 344, with a single suture 52 in each pouch 344. A mechanically operated pusher 346 can be located between roller assemblies 308, 312 to physically push suture 52 out of pouch 344, which splits open due to the force applied by pusher 346, to allow suture 52 to drop into bin 320 or bin 336.

Figure 13:
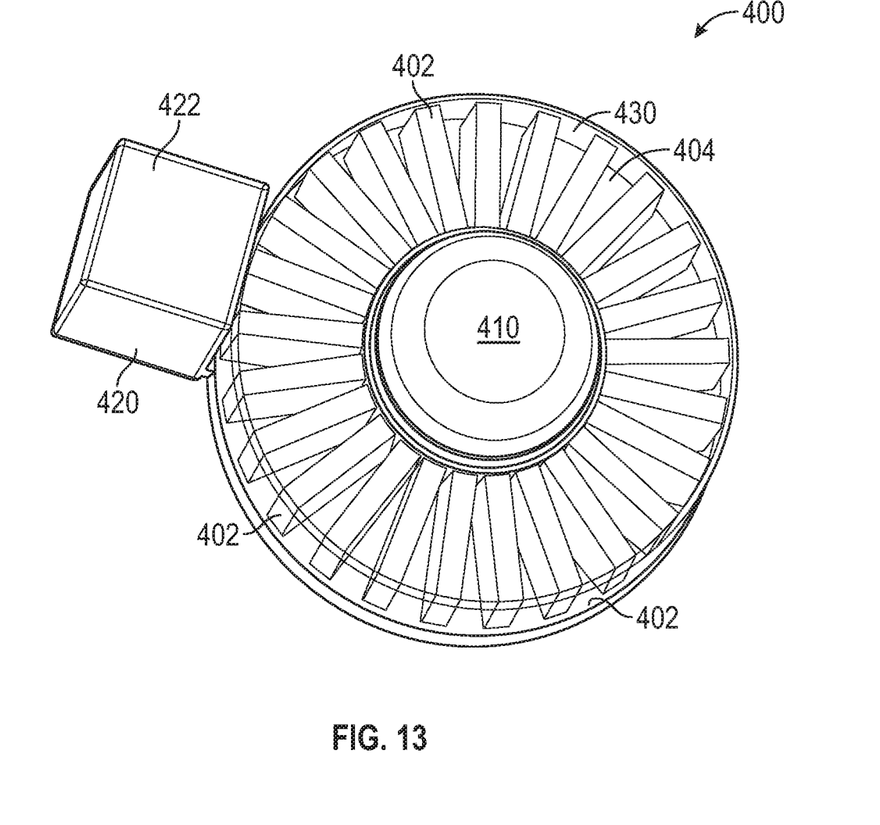
FIG. 13 is a perspective view of a suture storage, dispensing, and disposal device according to an alternative embodiment of the present invention.
Figure 13A:
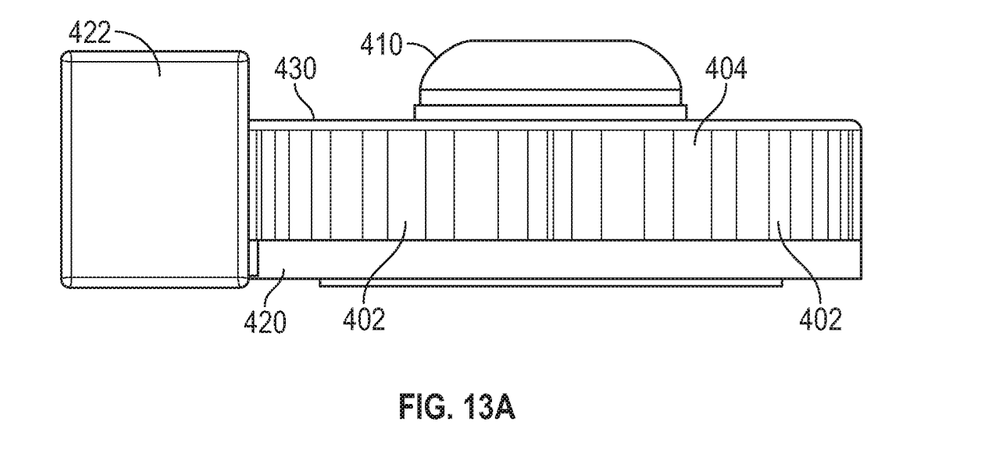
FIG. 13A is a front elevational view of the device of FIG. 13.

Referring now to FIGS. 13 and 13A, an alternative embodiment of a storage, dispensing, and disposal device 400 is shown. Device 400 is circular in design. While FIG. 13 shows that device 400 holds 25 dispensing bins 402 of sutures 52 or other items, those skilled in the art will recognize that more or less than 25 dispensing bins 402 can be provided.

Storage bin region 404 is able to rotate, thus enabling targeted selection of sutures 52 or other items for dispensing. A gear system (not shown) facilitates rotation of the internal storage bins 402. A central cylindrical region 410 is an exchangeable biohazards or sharps container for disposal; the internal bins 402 for dispensing rotate around the biohazards or sharps container 410.

A dispensing system 420 resides underneath and to the side of the internal storage feed bins 402. The design of the dispensing system 420 utilizes mechanisms already described above. A container 422 at the radius of dispensing system 420 contains the dispensing ports and all electronics, controllers, and control features to facilitate rotation and selection of the sutures 52 or other items. The storage feed bins 402 are easily filled by removing a top lid 430 and placing in new feed bins 402, sutures 52, or other items into bin region 404. The storage feed bins 402 are illustrated as rectangular bins as an example, and the storage feed bins 402 could also be shaped as cylinders, squares, pie shape, or other unique shapes. Device 400 is modular in component design and has the potential to be stackable, thus providing 25, 50, 75, or 100 different types of sutures 52 or other items for proper dispensing, counting, and disposal.

Although not shown, any of devices 100, 200, 300, 400 can be electrically powered via alternating current and/or via direct current using rechargeable or replaceable batteries either as a primary source of electrical power or as a back-up source of electrical power in the event of a loss of alternating current power.

Further, any of devices 100, 200, 300, 400 can be sterilized, such as by autoclaving. Alternatively, ultraviolet lights (not shown) can be located within each device 100, 200, 300, 400 and can be selectively operated to sterilize the interior of the respective device 100, 200, 300, 400.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A medical consumable storage, dispensing, and disposal device comprising:
   means for storing a plurality of new medical consumables therein;
   means for dispensing one of the plurality of new medical consumables; and
   means for storing a plurality of used medical consumables therein.

2. The medical consumable storage, dispensing, and disposal device according to claim 1, wherein the means for storing the plurality of medical consumables comprises storing each medical consumable in a sealed container.

3. The medical consumable storage, dispensing, and disposal device according to claim 1, wherein the means for storing the plurality of medical consumables comprises storing the medical consumables on a roll.

4. The medical consumable storage, dispensing, and disposal device according to claim 1, wherein the means for storing the plurality of medical consumables comprises biasing the medical consumables toward an extracting device.

5. The medical consumable storage, dispensing, and disposal device according to claim 3, wherein the means for dispensing the one of the plurality of new medical consumables comprises a means for opening a medical consumable package.

6. The medical consumable storage, dispensing, and disposal device according to claim 5, wherein the means for opening the medical consumable package further comprise a means for storing the opened medical consumable package.

7. The medical consumable storage, dispensing, and disposal device according to claim 6, further comprising a means for counting the plurality of used medical consumables therein.

8. The medical consumable storage, dispensing, and disposal device according to claim 7, further comprising a display for displaying a number of new medical consumables dispensed therefrom.

9. The medical consumable storage, dispensing, and disposal device according to claim 8, comprising a means for indicating when the plurality of used medical consumables does not equal the plurality of new medical consumables dispensed therefrom after a predetermined time.

10. A medical consumable storage, dispensing, and disposal device comprising:
a storage unit adapted to receive and store a plurality of medical consumables;
a dispensing unit configured to dispense each of the plurality of medical consumables, wherein the dispensing unit includes a counter that counts each of the plurality of medical consumables being dispensed from the dispensing unit; and
a disposal unit configured to dispose of each of the plurality of medical consumables.

11. The medical consumable storage, dispensing, and disposal device according to claim 10, wherein the dispensing unit is configured to dispense each of the plurality of medical consumables one at a time.

12. The medical consumable storage, dispensing, and disposal device according to claim 10, wherein the plurality of medical consumables are stored in a stack.

13. The medical consumable storage, dispensing, and disposal device according to claim 10, wherein the plurality of medical consumables are stored on a roll.

14. The medical consumable storage, dispensing, and disposal device according to claim 10, wherein the dispensing unit is configured to open a container containing one of the plurality of medical consumables.

15. The medical consumable storage, dispensing, and disposal device according to claim 10, wherein the disposal unit includes a first opening adapted to allow used medical consumables to be counted after being dropped into the first opening and a second opening not adapted to allow used medical consumables to be counted after being dropped into the second opening.

16. The medical consumable storage, dispensing, and disposal device according to claim 10, comprising a cover removably attached to the storage unit to provide access to the medical consumables in the storage unit.

17. The medical consumable storage, dispensing, and disposal device according to claim 10, wherein the disposal unit seals each of the plurality of medical consumables in individual used medical consumable packages.

18. The medical consumable storage, dispensing, and disposal device according to claim 17, wherein the disposal unit prints identifying indicia on each individual used medical consumable package.

* * * * *